(12) United States Patent
Shu et al.

(10) Patent No.: US 6,645,244 B2
(45) Date of Patent: *Nov. 11, 2003

(54) MECHANICAL HEART VALVE PROSTHESIS

(75) Inventors: Mark C. Shu, Mission Viego, CA (US); Jeffrey M. Gross, Rancho Santa Margarita, CA (US); Hong S. Shim, Santa Ana, CA (US)

(73) Assignee: Medtronic, Inc., Minneapolis, MN (US)

( * ) Notice: Subject to any disclaimer, the term of this patent is extended or adjusted under 35 U.S.C. 154(b) by 63 days.

This patent is subject to a terminal disclaimer.

(21) Appl. No.: 09/737,112

(22) Filed: Dec. 14, 2000

(65) Prior Publication Data

US 2001/0025197 A1 Sep. 27, 2001

Related U.S. Application Data

(63) Continuation of application No. 09/228,920, filed on Jan. 11, 1999, now abandoned, which is a continuation of application No. 08/898,144, filed on Jul. 22, 1997, now Pat. No. 5,919,226.

(51) Int. Cl.$^7$ .................................................. A61F 2/06
(52) U.S. Cl. ...................................................... 623/2.31
(58) Field of Search .............................. 623/2.31, 2.33, 623/2.1, 2.17, 2.18, 2.2, 2.22, 2.28, 2.38

(56) References Cited

U.S. PATENT DOCUMENTS

| | | | |
|---|---|---|---|
| 3,526,005 A | 9/1970 | Bokros et al. | 3/1 |
| 3,997,923 A | 12/1976 | Possis | 3/1.5 |
| 4,254,508 A | 3/1981 | Bokros | 3/1.5 |
| 4,276,658 A | 7/1981 | Hanson et al. | 3/1.5 |
| 4,306,319 A | 12/1981 | Kaster | 3/1.5 |
| RE31,040 E | 9/1982 | Possis | 3/1.5 |
| 4,689,046 A | 8/1987 | Bokros | 3/1.5 |
| 4,863,459 A | 9/1989 | Olin | 623/2 |
| 4,892,540 A | 1/1990 | Vallana | 623/2 |
| 5,178,632 A | 1/1993 | Hanson | 623/2 |
| 5,262,104 A | 11/1993 | Schwartz | 261/81 |
| 5,314,467 A | 5/1994 | Shu | 623/2 |
| 5,350,421 A | 9/1994 | Stupka et al. | |
| 5,354,330 A | 10/1994 | Hanson et al. | 623/2 |
| 5,522,886 A | 6/1996 | Milo | 623/2 |
| 5,545,216 A | 8/1996 | Bokros et al. | 623/2 |
| 5,641,324 A | 6/1997 | Bokros et al. | 623/2 |
| 5,772,694 A | 6/1998 | Bokros et al. | 623/2 |
| 5,824,062 A | 10/1998 | Patke et al. | 623/2 |

FOREIGN PATENT DOCUMENTS

| | | | |
|---|---|---|---|
| WO | WO 92/21305 | 12/1994 | A61F/2/24 |
| WO | WO 96/29957 | 10/1996 | A61F/2/24 |
| WO | WO 96/36299 | 11/1996 | A61F/2/24 |

OTHER PUBLICATIONS

Pivot Design In Bileaflet Valves ASAIO Journal 1992 (pp M600–M606) By F. Vallana et al.
Medical Carbon Research Institute, LLC / Technical Bulletin No. 0001 (pp1–8) ON–X Prosthetic Heart Valves (1996).
On–X Carbon Technical Bulletin 0002 Medical Carbon Research Institute LLC (991–6) 1996.
On–X Valves Medical Carbon Research Institute (undated).

*Primary Examiner*—David H. Willse
*Assistant Examiner*—Williams H Matthews
(74) *Attorney, Agent, or Firm*—Thomas G. Berry; Daniel W. Latham

(57) ABSTRACT

An improved artificial mechanical heart valve prosthesis having an improved leaflet hinge mechanism which improves washing of the hinge recess, reduces leaflet closing impact force and decreases noise and wear. A generally annular valve body having an annular interior surface extending between an inflow rim and an outflow rim thereof defines an annular orifice therethrough. A pair of leaflets are supported on said annular valve body for alternately blocking blood flow in an inflow direction when seated against the annular interior side wall in a closed position and then allowing the flow of blood through said annular orifice in a predetermined blood outflow direction when rotated into an open position.

19 Claims, 10 Drawing Sheets

MECHANICAL HEART VALVE PROSTHESIS

CROSS-REFERENCE TO RELATED APPLICATION

This application is a continuation of patent application Ser. No. 09/228,920, filed Jan. 11, 1999, abandoned, which is a continuation of Ser. No. 08/898,144, filed Jul. 22, 1997, now U.S. Pat. No. 5,919,226.

FIELD OF THE INVENTION

The present invention pertains to prosthetic mechanical heart valves and in particular, to a bi-leaflet mechanical valve with an improved pivoting mechanism.

BACKGROUND OF THE INVENTION

During each cardiac cycle, the natural heart valves selectively open to allow blood to flow through them and then close to block blood flow. During systole, the mitral and tricuspid valves close to prevent reverse blood flow from the ventricles to the atria. At the same time, the aortic and pulmonary valves open to allow blood flow into the aorta and pulmonary arteries. Conversely, during diastole, the aortic and pulmonary valves close to prevent reverse blood flow from the aorta and pulmonary arteries into the ventricles, and the mitral and tricuspid valves open to allow blood flow into the ventricles. The cardiac valves open and close passively in response to blood pressure changes operating against the valve leaflet structure. Their valve leaflets close when forward pressure gradient reverses and urges blood flow backward and open when forward pressure gradient urges blood flow forward.

In certain individuals, the performance of a natural heart valve is compromised due to a birth defect or becomes compromised due to various disease processes. Surgical repair or replacement of the natural heart valve is considered when the natural heart valve is impaired to an extent such that normal cardiac function cannot be maintained. The natural heart valve can be replaced by homograft valves obtained from the same species (e.g., human donor heart valves), heterograft valves acquired from different species, and prosthetic mechanical heart valves.

The present invention is directed to improvements in prosthetic mechanical heart valves. Modern implantable mechanical heart valves are typically formed of a relatively rigid, generally annular valve body defining a blood flow orifice and an annular valve seat and one or more occluders that are movable between a closed, seated position in the annular valve seat and an open position at an angle to the valve body axis. These components of mechanical heart valves are made of blood compatible, non-thrombogenic materials, i.e., pyrolytic carbon and titanium. A biocompatible, fabric sewing ring is typically provided around the exterior of the valve body to provide an attachment site for suturing the valve prosthesis into a prepared valve annulus. The occluder(s) is retained and a prescribed range of motion is defined by a cooperating hinge mechanism or other restraining mechanism. Such prosthetic heart valves function essentially as check valves in which the occluder(s) responds to changes in the relative blood pressure in the forward and reverse directions as described above and move between their open and closed positions.

A wide variety of mechanical heart valve designs have been proposed and/or utilized in the past. For example, an early clinically used mechanical heart valve employed a spherical ball moving into and out of engagement with an annular seat within a cage in response to the normal pumping action of the heart. Other clinically used heart valve prostheses have employed occluders in the form of a circular disc that pivots open and closed in response to blood pressure changes while being restrained by cooperative structure of the valve body.

A further clinically used bi-leaflet heart valve prosthesis employs a pair of semi-circular or semi-elliptical plates or leaflets that hinge open and closed together. Such bi-leaflet heart valves are typically entirely formed with a pyrolytic carbon or with pyrolytic carbon coating on all exterior surfaces of the valve body and leaflets. A typical method of coating pyrolytic carbon onto a valve substrate is disclosed in U.S. Pat. No. 3,526,005. The pyrolytic carbon coating provides wear resistant surface, and provides insurance against thrombus formation on such surfaces.

Bi-leaflet heart valves generally utilize pivot or hinge mechanisms to guide and control the motion of the leaflets between the seated, closed position and the open position. In such design configurations, two mirror image leaflets are typically disposed in opposed or mirror image relation to one another. Upon closure, each valve leaflet occludes or covers half of the annular valve orifice or valve annulus. Generally, each leaflet is designed with roughly semicircular shape and has a rounded exterior margin and peripheral edge which engages an inner seat surface of the valve body to provide a peripheral seal, and an inner, diametrically extending edge and adjacent margins adapted to abut against the counterpart edges and margins on the other leaflet. Each leaflet can rotate about an axis defined by a pair of opposed hinge pivot points in opposed hinge recesses that are offset from the central axis of the valve annulus. The leaflets are typically flat, but curved or elliptical leaflets have been proposed.

Such mechanical heart valves are typically designed in somewhat differing profile configurations for replacement of differing impaired natural heart valves. However, the basic in vivo operating principle is similar regardless of configuration. Using an aortic valve as an example, when blood pressure rises in response to left ventricle contraction or systole in each cardiac cycle, the leaflets of such a valve pivot from a closed position to an open position to permit blood flow past the leaflets. When the left ventricle contraction is complete, blood tends to flow in the opposite direction in diastole in response to the back pressure. The back pressure causes the aortic valve leaflets to close in order to maintain arterial pressure in the arterial system.

The most widely accepted type of bi-leaflet heart valve presently used mounts its leaflets for pivoting movement by means of a pair of rounded ears extending radially outwardly from opposed edges of the leaflets to fit within rounded hinge recesses in opposed flat surfaces of the valve body side wall. Such bi-leaflet valves are exemplified by the mitral valve depicted in U.S. Pat. No. 4,276,658 and the aortic heart valve depicted in U.S. Pat. No. 5,178,632, both incorporated herein by reference.

The leaflet ears are received within curved hinge recesses extending radially into opposed flat surfaces of thickened wall sections inside the annulus of the generally cylindrical or annular valve body. Each hinge recess is designed in at least one respect to match the shape of the leaflet ear and is bounded by sets of leaflet stop surfaces angled to define the extreme open and closed leaflet positions. In other words, where the ear is formed as a portion of a circle having a given radius, the counterpart hinge recess is formed as a semicircle having a slightly greater radius. An inverse arrangement of the ear and recess hinge mechanism is depicted in U.S. Pat. No. 5,354,330, incorporated herein by reference, whereby the leaflet ear is replaced by a leaflet recess, and the hinge recess is replaced by a complementary shaped hinge boss.

To achieve the pivoting mechanism, the mating surfaces of the ears and recesses are precisely machined so as to provide a small but definite working clearance for the ears to pivot about the necked down pivot surface and be retained within the hinge recesses. During valve assembly, the annular valve body is deformed or distended so that the leaflet ears may be inserted into the respective hinge recesses. Each manufactured heart valve is then lab tested "dry" to ensure that the leaflets are held tightly enough to be secure against falling out of their hinge recesses, but are not so tightly engaged so as to create a binding or restricted valve action.

The range of leaflet motion is typically controlled by pins or ramps or opposed side stops of the hinge recesses or by hinge bosses in the valve body. In one format described in the above-incorporated '632 patent, the hinge recess is generally spherical and bounded by open and closed stop surfaces of a stop member projecting into the recess. In the other formats depicted in the above-incorporated, '658 and '046 patents, each hinge recess has an elongated "bow-tie" or "butterfly" appearance created by the inward angulation of opposed side edges extending from inflow and outflow end edges and meeting at opposite disposed, necked down, pivot points or surfaces intermediate the end edges.

A great deal of effort has been devoted to controlling the range of movement and the acceleration of the leaflets between the open and closed positions to both control noise and decrease wear or the possibility of leaflet fracture. In the past, bi-leaflet valves were known to be noisy, in the sense that patients could frequently hear the seating of the valve leaflet peripheral edges against the valve seats when they closed. It is desirable for patient comfort to provide a bi-leaflet design that minimizes the distraction of leaflet seating noise.

It is also known that blood cells are extremely fragile and delicate and can be damaged and/or destroyed when trapped in the valve seat during closure of the valve leaflet or in the wiping area of the valve leaflet ears and hinge recesses or between the leaflet ears and the open and closed stop surfaces. The wiping areas of the hinge recesses have the highest potential of thrombus formation and emboli entrapment which can accumulate therein, impair the movement of the valve leaflets, and result in valve failure requiring surgical intervention. The close tolerances and resulting narrow gaps between the leaflet ears and the hinge recess surfaces contribute to this problem. During the open leaflet phase, blood barely flows through the recess under very low forward pressure gradient. During the closed leaflet phase, blood flow in the hinge recess region is, of course, stopped. Any existing thrombus and/or entrapped emboli in the hinge recess can restrict leaflet motion, which in turn can further enhance thrombus formation and trapping more emboli. To this time, no design has been successful in eradicating this problem. Consequently, patients receiving current bi-leaflet mechanical heart valves are prescribed continuous blood anticoagulation therapy to prevent thrombus formation and thromboemboli.

In this regard, in prior art bi-leaflet prosthetic heart valves described above employing the generally concave hinge recesses formed in planar surfaces to receive generally convex leaflet ears, the side walls that stop movement of the leaflet ears and define the leaflet open and closed positions are designed to be orthogonally cut into the planar surfaces, resulting in relatively abrupt or "sharp" edges with the planar surface. This configuration allows relatively large areas of contact between the sides of the valve ears and the recess side walls in the open and closed leaflet positions. The hinge recess end boundaries or edges extending between the ends of the side walls in the inflow and outflow directions are also designed with relatively sharp transitions at the planar surfaces. Relatively sharp corners are created at the junctions of the ends of the side walls and the ends of the inflow and outflow recess end edges. These sharp edges and corners create unnecessary blood flow stagnation regions and blood flow separations. The sharp edges and corners are also high mechanical stress concentration sites and may also be potential structural failure initiation sites.

In spite of significant advances which have taken place in the construction of mechanical heart valves, there is still room for significant improvements therein to minimize flow stagnation regions inside the valve annulus, especially in the hinge recesses, which may lead to thrombus formation and cause the failure of a prosthetic valve, to reduce impact force upon valve closure, and to eliminate flow turbulence in or near valve annulus.

This invention is therefore directed to improving the current hinge mechanisms employed in bi-leaflet prosthetic mechanical heart valves to increase blood washing of the hinge recess, improve valve hemodynamic performance, and to reduce leaflet impact force, valve failure potential, and the need for long term anticoagulant therapy.

SUMMARY OF THE INVENTION

Therefore, it is a primary object of the present invention to provide an improved mechanical heart valve prosthesis that provides improved performance while responding hemodynamically to the normal pumping action of the heart.

It is another object of the present invention to provide an improved heart valve prosthesis that reduces exposure of blood and its constituents to substantial mechanical forces and stresses, thereby reducing the likelihood of damage to constituents and cells found within human blood.

It is an additional object of the present invention to eliminate sharp boundaries or edges and corners where the end edges meet the side edges to avoid blood cell damage and to minimize potential mechanical failure initiation sites in the hinge recess.

It is a further object of the present invention to provide an improved heart valve prosthesis with mechanical design features and characteristics that reduce the occurrence of a concentration of mechanical stresses at given locations in the device.

It is yet a further object of the present invention to provide an improved heart valve prosthesis that enhances the uniformity of blood flow through the device so as to substantially reduce the creation of zones of stasis or stagnation within the device and its environs.

The designs of all mechanical, bi-leaflet prosthetic heart valves currently in clinical use ignore the differences in fluid dynamic forces acting on the leaflets between the opening phase and the closing phase. The contacting or bearing surfaces of the leaflet ear and hinge recess are typically symmetric and are simply designed to operate the same in both phases. The dynamic force applied to the leaflets in the valve closing phase is one to two orders of magnitude higher than that in the valve opening phase. We have realized that the hinge recess and matching leaflet ear should be designed so that the bearing surfaces in the inflow open phase and the outflow closing phase have differing configurations to account for and utilize the dynamic force difference. In accordance with the present invention, this dynamic force difference is taken into account, resulting in a hinge recess design having distinct features of the inflow and outflow portions thereof. These features include distinct inflow and outflow recess profiles and surface areas, differing side wall lengths, and differing inflow and outflow recess end edge heights.

In particular, in a first aspect of the present invention applicable to each hinge mechanism formed in opposed planar surface regions of the valve body interior wall, a relatively shallow inflow or entrance ramp is achieved in the hinge recess. A convexly curved inflow transition surface extends from the planar surface at the arcuate inflow hinge recess end boundary or edge into the generally concave inflow recess bearing surface. A relatively more open outflow or exit ramp is also employed through use of a further convexly curved outflow transition surface at the junction of the outflow recess bearing surface with the arcuate outflow hinge recess end boundary or edge. Moreover, a relatively recessed outflow flat in the relatively planar surface that the hinge recess is formed in extends in the outflow direction away from the arcuate outflow hinge recess end edge. The resulting recess bearing surface profile and the profile of the leaflet ear bearing edge contribute to favorable operation of the improved hinge configuration improving the blood flow dynamics, reducing areas of stasis, and reducing eddies in the blood flow pattern through the valve annular orifice.

The valve leaflet hinge mechanisms are preferably shaped to account for the differing separation distances between the planar surfaces at the inflow hinge recess end edge and the outflow flats at the outflow hinge recess end edges. To this end, the leaflet peripheral edge further comprises first and second relatively straight outflow shoulders extending between the opposite ends of the major arcuate peripheral edge of the leaflet and the ear bearing edge of the first and second leaflet ears, respectively, whereby the first and second outflow shoulders are separated apart by a distance somewhat less than the distance between the opposed outflow flats. Similarly, first and second relatively straight inflow shoulders extend between the opposite ends of the straight edge of the leaflet and the ear bearing edge of the first and second leaflet ears, respectively, whereby the first and second inflow shoulders are separated apart by a second distance less than the first distance and somewhat less than the distance between the opposed planar surfaces.

In addition, in a further aspect of the present invention, the relatively sharp or acute closed, and, optionally, open stop side edges of the hinge recess are replaced by convex stop edges at the junction of each side wall with the planar surface. The convex stop edge shape results in a contact band portion of each recess side wall projecting into each recess inflow and outflow portion to minimize the contact area with like contact band portions of the leaflet ear inflow and outflow sides. This reduces the total area of contact between each side wall and leaflet ear side, thereby reducing damage to blood cells in the contact region.

In a still further aspect of the present invention, the valve body is shaped to be generally annular with an annular interior side wall generally extending between an inflow rim and an outflow rim thereof. The annular valve body defines an annular blood flow orifice having a central blood flow axis centrally located with respect to the annular interior surface. A generally convex outflow rim transition surface extends in a band between the outflow rim and the annular interior side wall having a first radius of curvature. A generally convex inflow rim transition surface extends in a band between the inflow rim and the annular interior side wall having a second radius of curvature greater than the first radius of curvature. The inflow rim transition surface directs blood flow away from the annular interior surface and centrally through the annular orifice when the occluder means is in the open position.

In yet another aspect of the present invention, the parallel disposed and inwardly facing, opposed planar surfaces formed along the annular interior surface of the annular valve body are each bounded by planar surface side edges and planar surface inflow and outflow edges. The oppositely disposed of hinge recesses are each formed in one of the opposed planar surfaces for cooperatively engaging leaflet ears and for guiding movement of the leaflet ears between the leaflet open and closed positions. A planar inflow chamfer extends from the inflow rim to the planar surface inflow edge to deflect any blood components susceptible of damage by operation of the leaflet ears in the hinge recesses centrally through the annular orifice during blood flow therethrough.

In the preferred embodiments, the annular valve body includes a pair of such valve leaflets and respective pairs of hinge mechanisms for pivoting between open and seated, closed positions, thereby allowing a unidirectional flow of blood through the passageway in the open position during the cardiac cycle. The four hinge recesses are arranged in a mirror image relationship of oppositely disposed hinge recess pairs with respect to a pair of arcuate seats in respective halves of the valve body. The spacing apart of the oppositely disposed pairs of the hinge recesses provides for an optimized ratio of the central flow orifice between the two open leaflets in comparison to the two side flow orifices.

Each of the hinge recesses is butterfly or bow-tie shaped in outline, the outline defined by the arcuate inflow and outflow hinge recess end boundaries or edges that are separated by inflow and outflow pairs of opposed open and closed, stop side walls. The recess inflow and outflow side wall pairs extending toward one another are angled inward to centrally disposed, inflow and outflow pivots about which the valve leaflet ear (and the leaflet as a whole) pivots during the opening and closing phases.

The opposed pairs of elongated, butterfly or bow-tie shaped hinge recesses are generally angled, end-to-end, at common, and complementary, reference angles of inclination with respect to the center axis of the valve annulus. Each such reference angle of inclination is intermediate a maximum open angle of inclination of the open side wall and a maximum closed or seated angle of inclination of the closed side wall.

The inflow portion of the hinge recess in the planar surface extends from the inflow end edge and toward the pivot points and has a wide inflow mouth defined by the side edges thereof that diverge away from one another with distance from the pivot points and an inflow recess bearing surface. The inflow recess bearing surface is shaped from the inflow end edge to define an entrance ramp in the inflow portion to admit blood flow into the hinge recess in the inflow direction. The entrance ramp slope allows good blood flow washing function in this inflow portion of the hinge recess while the inflow recess bearing surface is wiped as the valve leaflet ear sweeps over it in pivoting between the open and closed positions.

The design of the hinge recess also provides controlled pivoting and translation guidance to the movement of a valve leaflet into the closed and seated position. This allows a leaflet to change its rotating axis near its closed position and reduce its tangential velocity at the leaflet major radius. The reduction in velocity reduces impact force of contact of the leaflet's peripheral seat edge with the valve seat in the valve body. This reduced impact force prolongs the heart valve's fatigue life, and reduces the propensity of cavitation and valve closing noise. The large surface area of contact of the leaflet ear bearing edge with the inflow portion of the hinge recess reduces concentrated valve closing stress on the hinge recess.

The outflow portion of the hinge recess extends between the centrally disposed pivot points and the outflow end of the recess, and the outflow bearing surface in the outflow portion is asymmetric in contour with respect to the inflow bearing surface. The side edges of the recess also diverge apart from the centrally disposed pivot points to the point where they meet the arcuate outflow end edge.

The decreased height of the junction of the outflow hinge recess end edge with the outflow flat allows blood funneled into the hinge recess in the inflow direction to more readily flow out again into the outflow flat in the outflow direction. The convexly shaped leaflet ears projecting into the hinge recesses allow the leaflet to pivot between the open and closed positions and sweep the outer edges of the leaflet ears over the recess bearing surface and flush blood components from the hinge recesses and into the outflow flats and from the outflow flats through the annular orifice of the heart valve. This open exit takes advantage of a much smaller dynamic drag force acting on the opposed flat leaflet surfaces during the valve opening phase than exist during the valve closing phase. Any blood components located within the hinge recess can be easily washed out by the blood flow in both the inflow and outflow directions while the leaflet ears sweep across the inflow and outflow portions of the hinge recess base in both the opening and closing directions.

BRIEF DESCRIPTION OF THE DRAWINGS

These and other objects, advantages and features of the present invention will be appreciated as the same becomes better understood by reference to the following detailed description of the preferred embodiment of the invention when considered in connection with the accompanying drawings, in which like numbered reference numbers designate like parts throughout the figures thereof, and wherein.

DETAILED DESCRIPTION OF THE PREFERRED EMBODIMENTS OF THE INVENTION

While it will be understood that the present invention may be embodied in heart valves having occluder(s) formed of one or two leaflets, or conceivably three or more leaflets, a detailed description will be given of a preferred form of valve wherein there are two leaflets which swing between open and closed positions, and which leaflets have their inner diametrical side edges substantially abutting each other in the closed position of the valve and with the leaflet ears forming portions of the pivot mechanisms being offset slightly away from these edges. The preferred embodiment of the present invention is also described having relatively planar valve leaflets, and it will be understood that the principles of the present invention may be implemented in mechanical heart valves that are not planar e.g., curved leaflets. Moreover, while the preferred embodiment of the present invention is implemented in a hinge mechanism employing generally convex leaflet ears and concave hinge recesses, it will be understood that the principles of the present invention may be implemented into a valve hinge mechanism that is configured in an inverse relationship of the leaflet ear and hinge recesses. In addition, the preferred embodiment of the present invention implements two features of the present invention that may be independently employed or optimally combined as described hereafter.

Figure 1:
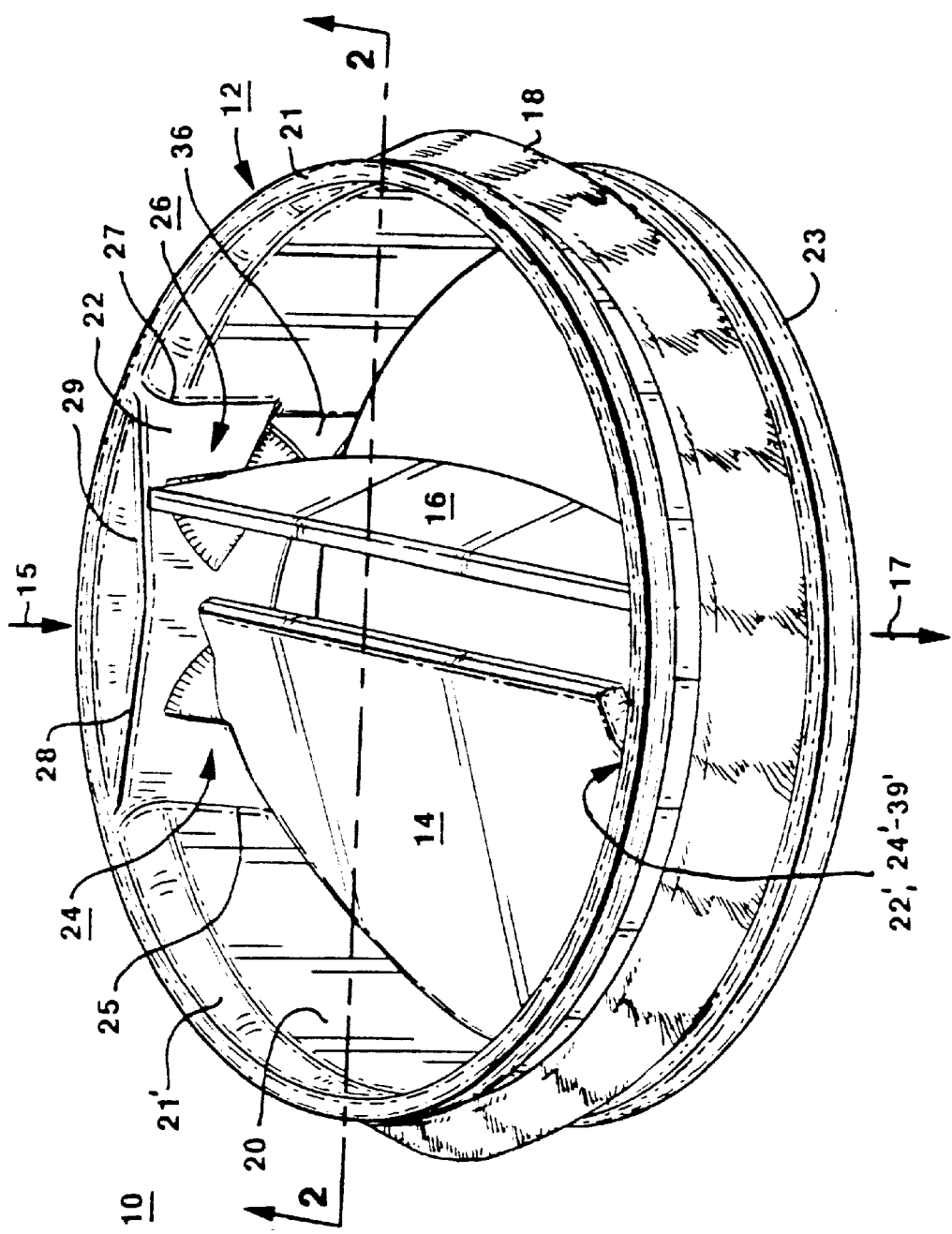
FIG. 1 is an isometric view from the inflow side of a bi-leaflet mechanical heart valve in an aortic configuration incorporating the improved blood flow characteristics of the present invention.

Referring now to the drawings in greater detail, FIG. 1 shows a mechanical heart valve prosthesis or heart valve 10 in an aortic valve configuration having a low, narrow profile in accordance with a preferred embodiment of the invention. The heart valve 10 includes four major components, that is, an annular valve body 12, an occluder comprising first and second leaflets 14 and 16, and a fabric sewing ring 18. The first and second leaflets 14 and 16 are depicted in the closed, seated position and the open position, respectively, simply to illustrate the range of motion of the leaflets between these extreme positions. When in the closed position, the generally semicircular peripheral leaflet edges are seated in contact with respective valve seat regions extending around respective halves of the annular valve body 12, and their straight peripheral edges extending between the opposed leaflet ears contact one another at the centerline of the valve annulus.

The fabric sewing ring 18 (shown not necessarily to scale) may take any of the forms known in the art and is preferably rotatable about an outer sewing ring channel formed in the outer wall of the annular valve body 12 between exterior flanges of the annular, inflow and outflow rims 21 and 23. The details of the construction, retention, and use of the sewing ring 18 are not important to the present invention, and may take any of the known forms. Preferably, the valve body 12 may be formed of machined and polished titanium or of pyrolytic carbon or of a graphite substrate coated with pyrolytic carbon in a manner well known in the art of mechanical heart valve fabrication. Similarly, the valve leaflets 14 and 16 are preferably formed of a graphite substrate coated with pyrolytic carbon in a manner well known in the art.

Figure 2:
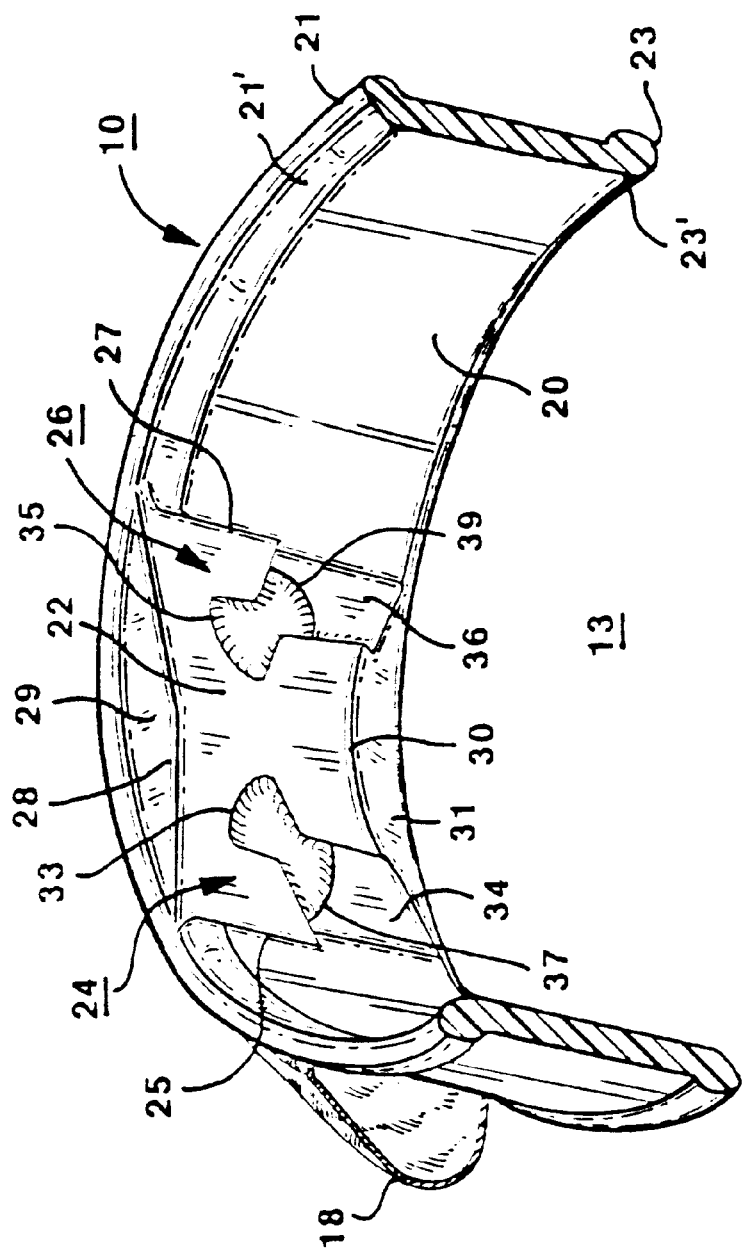
FIGS. 2 and 3 are isometric and elevation cross-section views of the half of the annular valve body taken along lines 2—2 of FIG. 1 depicting the hinge recess and associated outflow flat of the present invention in a planar surface of a thickened portion of the annular valve body.
Figure 3:
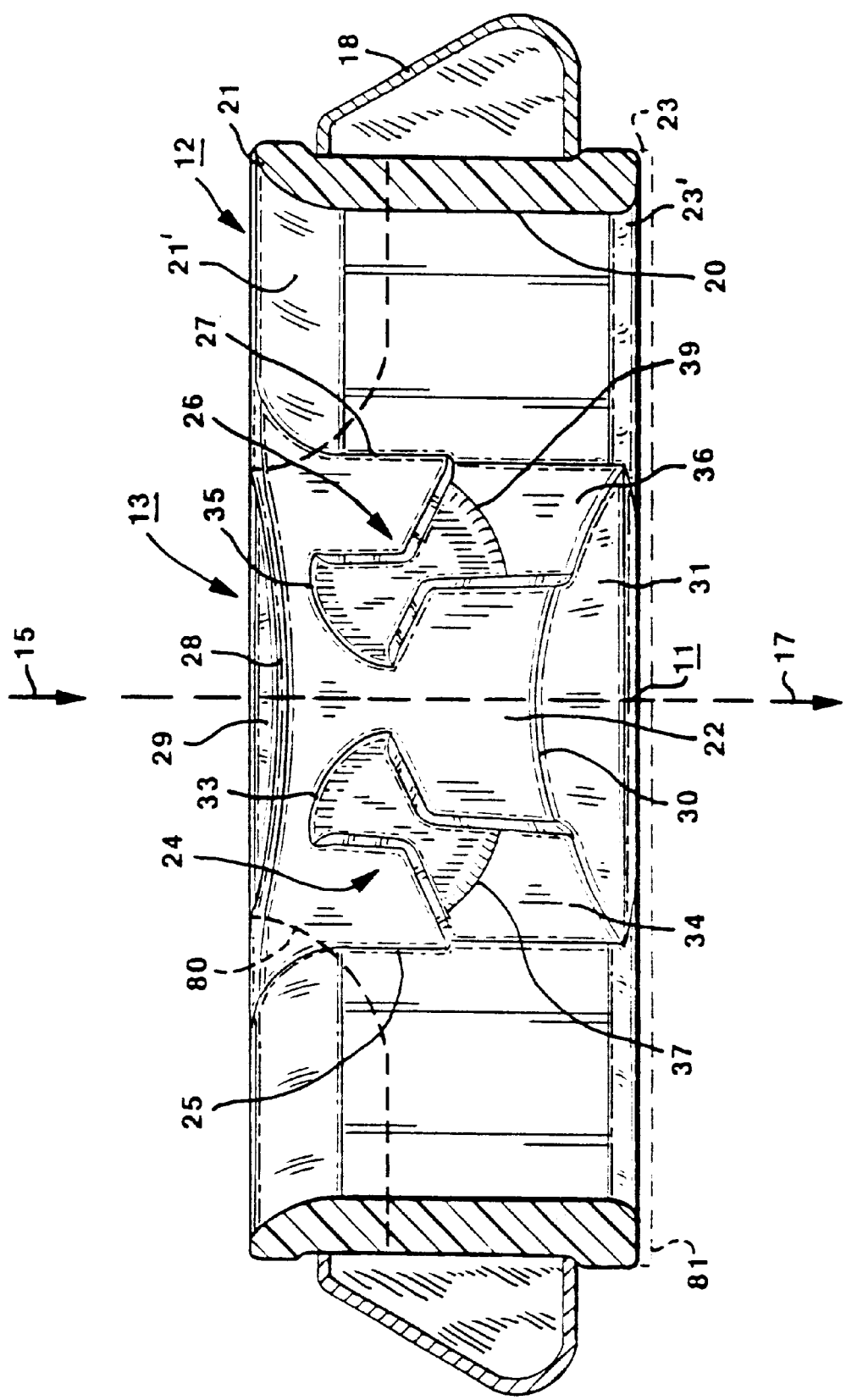

The heart valve 10 has a plane of symmetry extending through its midsection defined as coincident with the central axis 11 of blood flow through the annulus or annular orifice 13 of the valve body 12 and extending equidistantly between the parallel edges of the leaflets 14, 16 (as best seen in the cross-section view of FIG. 3). The heart valve 10 is to be implanted so that forward blood flow is downward in FIGS. 1–4 defining an inflow side and inflow blood direction 15 and an outflow side and outflow blood direction 17 of the heart valve 10. An increase in blood pressure on the inflow side over the blood pressure on the outflow side causes both of the leaflets 14, 16 to swing open from the seated position of leaflet 14 to the open position of leaflet 16. Conversely, when the relative blood pressure reverses, the back pressure on the outflow side causes the leaflets 14, 16 to swing closed from the open position to the closed position of leaflet 14.

Figure 4:
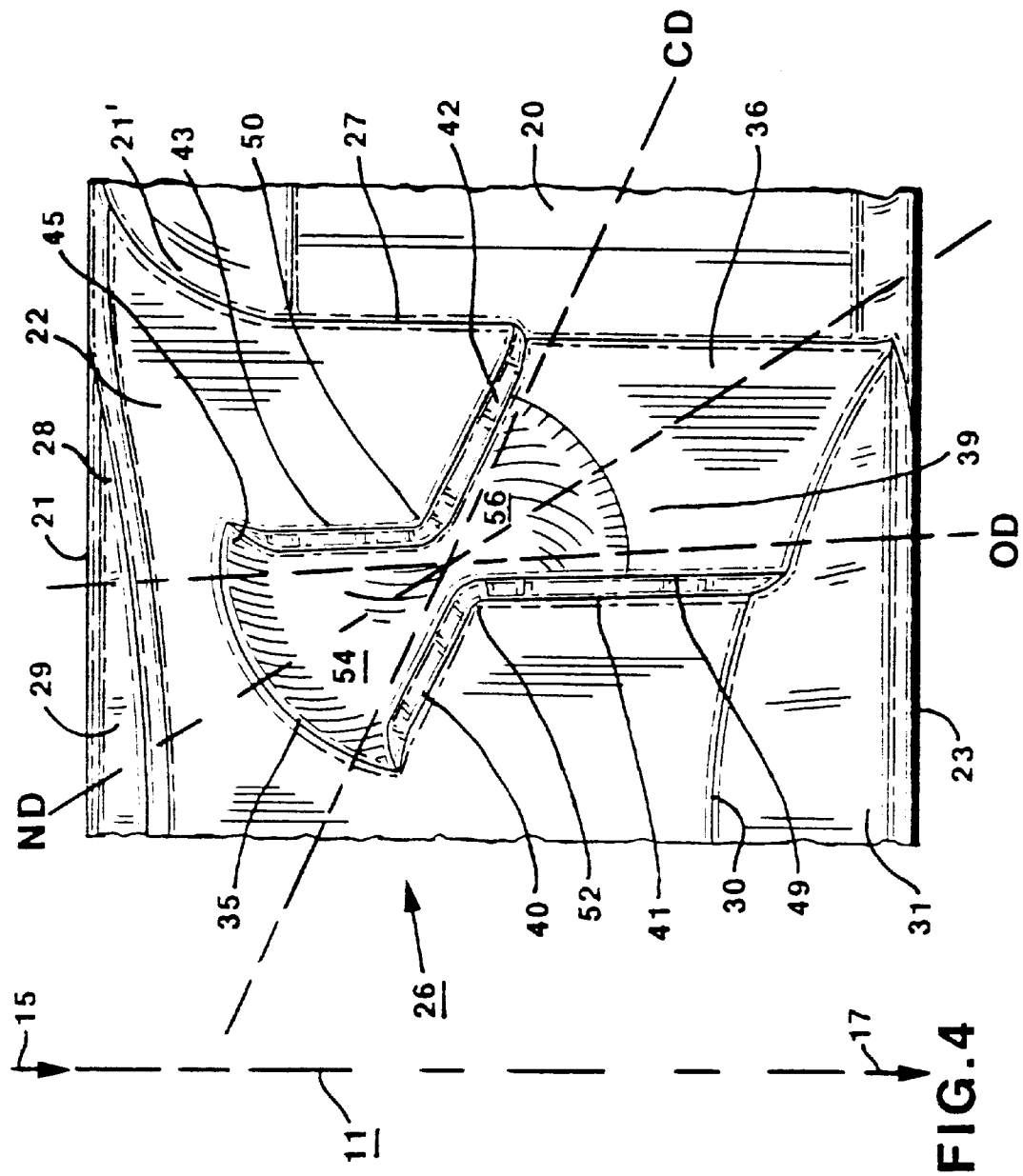
FIG. 4 is an expanded view of an exemplary hinge recess and outflow flat of FIGS. 2 and 3 showing details of the hinge recess and the angles of inclination of the associated planar valve leaflet in the open, closed and a nominal transition position thereof with respect to the valve annulus centerline.

The annular valve body 12 is shown by itself and in cross-section in FIGS. 2 and 3 and in the detail view of FIG. 4 to expose the features of the hinge recess of the present invention. The valve leaflets 14, 16 are constructed in mirror image fashion, and the valve features that cooperate with the hinge recess and the annular interior side wall 20 are depicted in greater detail in FIGS. 5–7. Each valve leaflet 14, 16 has generally opposed major planar inflow and outflow side surfaces and a continuous, peripheral seat edge extending between the opposed major surfaces and beveled to seat against a corresponding arcuate seat region of the annular interior side wall 20 of the annular valve body 12 in the closed position. Each valve leaflet 14, 16 is also formed with a pair of convexly projecting leaflet ears at opposed locations along the opposite ends of the peripheral seat edge and the opposite ends of a straight edge of the valve leaflet.

The annular valve body 12 includes a generally continuous, circular interior side wall 20 intermediate the inflow and outflow rims 21 and 23 defining a valve annulus of a predetermined diameter. The interior side wall 20 is thickened in two diametrically opposed formations and have major planar surfaces 22, 22' that are generally mirror images of one another and are preferably parallel to one another and bounded by planar surface edges. The planar surface 22 intersects the curved surface of the interior side wall 20 along planar surface side edges 25 and 27. The planar surface 22 is bounded on the inflow and outflow sides by concave planar surface inflow and outflow edges 28 and 30 that extend concavely inwardly from inflow and outflow rims 21 and 23, respectively. Respective inflow and outflow chamfers 29 and 31 are formed between the concave inflow edge 28 and inflow rim 21 and between the concave outflow edge 30 and outflow rim 23. The planar surface 22' is formed and bounded in the identical, mirror image manner as planar surface 22.

The planar surfaces 22, 22' of these formations each have a pair of hinge recesses 24, 26 and 24', 26' formed therein such that the hinge recesses 24, 24' and 26, 26' are diametrically opposed to one another across the annular orifice 13. Each hinge recess 24, 24', 26, 26' extends concavely outwardly from each planar surface 22, 22' and into the thickened formation of the annular body interior side wall 20. Each hinge recess 24, 24', 26, 26' is shaped in recess depth to form a pivot bearing surface for receiving a convexly projecting ear bearing edge of a valve leaflet 14, 16. Each hinge recess of the hinge recess pairs 24, 24' and 26, 26' has opposed recess side edges shaped and oriented to allow and bound movement of the respective valve leaflet 14, 16 between the open and closed positions. The hinge recesses 24 and 26 have arcuate inflow hinge recess end edges 33 and 35 and outflow hinge recess end edges 37 and 39, respectively.

In accordance with one aspect of the present invention, outflow flats 34, 36 and 34', 36', are recessed into planar surfaces 22 and 22', respectively. The outflow flats 34, 36 and 34', 36' extend in the outflow direction from outflow hinge recess end edges 33, 35 and 33', 35' and to the planar surface concave outflow edges 30, 30'. The outflow flats 34, 36 and 34', 36' also terminate at extensions of the side edges 25, 27 and 25', 27', respectively, of the planar surfaces 22, 22'. The bearing surfaces and stop side edges of the convexly shaped leaflet ears and the hinge recesses 24, 24' and 26, 26' allow and control the pivotal movement of the leaflets 14 and 16 between the open and closed positions. As the leaflets 14 and 16 pivot, the bearing edges of the leaflet ears sweep over the concave bearing surfaces of the hinge recesses 24, 24' and 26, 26' and flush blood components from the hinge recesses 24, 24' and 26, 26' into the outflow flats 34, 34' and 36, 36' and from the outflow flats 34, 34' and 36, 36' through the annular orifice 13 in the outflow direction 17.

The particular configuration of all of the hinge recesses is shown in greater detail in the representative expanded view of hinge recess 26 of FIG. 4. The butterfly or bow-tie outline shape of the exemplary hinge recess 26 is effected by the inflow hinge recess end edge 35 extending arcuately between inflow ends of the inflow, open stop, side wall 43 and outflow, closed stop, side wall 40, the outflow hinge recess end edge 39 extending arcuately between outflow ends of the inflow, closed stop, side wall 42 and outflow, open stop, side wall 41, and the opposed, centrally disposed, inflow or closing pivot 50 and outflow or opening pivot 52. The inflow, open stop, side wall 43 and the outflow, open stop, side wall 41 extend in parallel to one another along the open leaflet angle of inclination OD and are spaced apart to accommodate the thickness of a leaflet ear. Similarly, the inflow, closed stop, side wall 42 and the outflow, closed stop, side wall 40 extend in parallel to one another along the closed or seated leaflet angle of inclination CD and are spaced apart to accommodate the thickness of a leaflet ear. FIG. 4 also depicts the nominal, end-to-end, angular inclination of the hinge recess 26 along line ND that also constitutes an imaginary centerline of the hinge recess 26. The angles of inclination CD, OD and ND also represent imaginary center lines of the leaflet 16 in the closed, open and nominal transition leaflet positions, respectively.

Each set of the open and closed stop, recess side walls 41, 43 and 40, 42 of hinge recesses 26, 26' are angled in parallel and define the open and closed leaflet angular directions for the opposed leaflet ears of the second leaflet 16. In other words, each opposed pair of elongated, butterfly or bow-tie shaped hinge recesses 26, 26' is generally angled, end-to-end, at common angles of inclination CD, OD and ND with respect to the centerline 11 of the valve annular orifice 13. The other pair of hinge recesses 24, 24' receiving the leaflet ears of the first leaflet 14 are also generally angled at complementary closed, open and nominal angles of inclination with respect to the centerline 11 of the valve annular orifice 13.

The inflow hinge recess bearing surface 54 extends from the arcuate inflow hinge recess end edge 35 toward the intermediate hinge recess bearing surface 56 between the pivot points 50 and 52. Similarly, the outflow hinge recess bearing surface 58 extends from the arcuate outflow hinge recess end edge 39 toward the intermediate hinge recess bearing surface 56 between the pivot points 50, 52. As described further below, in reference to FIG. 8, the intermediate hinge recess bearing surface 56 is generally the deepest portion of the hinge recess 26, and the outflow hinge recess end edge 39 is recessed lower than the inflow hinge recess end edge 35.

Figure 9:
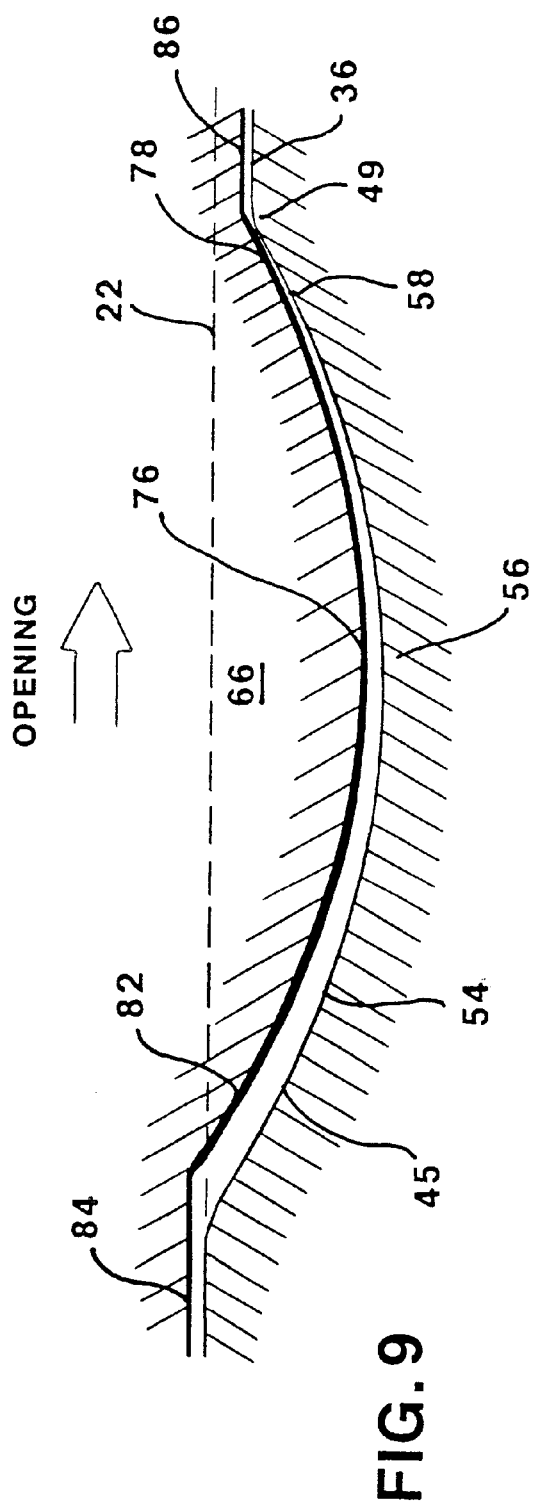
FIG. 9 is an elevation profile depicting a leaflet ear bearing against the hinge recess bearing surfaces taken in the opening phase of the valve leaflet.
Figure 10:
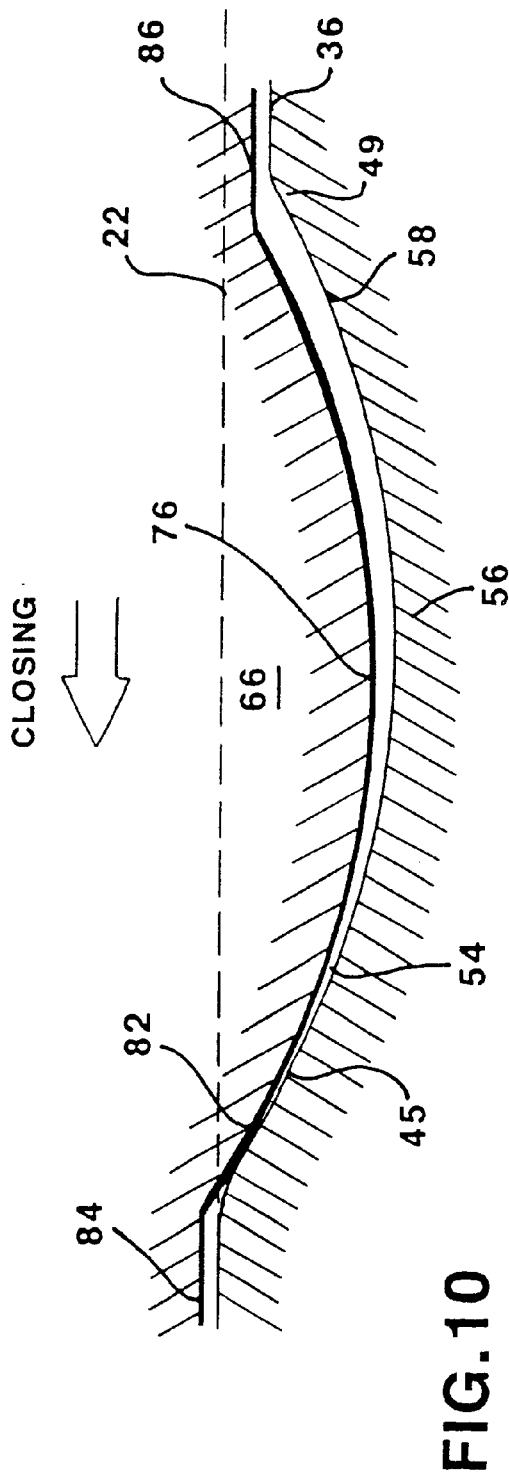
FIG. 10 is an elevation profile depicting a leaflet ear bearing against the hinge recess bearing surfaces taken in the closing phase of the valve leaflet.

The lengths of the outflow, closed stop, side wall 40 and the inflow, open stop, side wall 43 measured from the pivot points 50 and 52, respectively, Preferably exceed the lengths of the inflow, closed stop, side wall 42 and the outflow, open stop, side wall 41 measured from the pivot points 50 and 52. The inflow hinge recess end edge 35 is therefore longer than the outflow recess end edge 39. The inflow hinge recess bearing surface 54 is therefore larger in surface area than the outflow hinge recess bearing surface 58. The greater area of the inflow recess bearing surface 54 is useful for absorbing loading forces during the closing phase of the leaflet as shown in FIG. 10, described below. The smaller area of the outflow bearing surface 58 is useful to reduce resistance to blood flow during the opening phase of the leaflet as shown in FIG. 9, described below.

As shown in FIG. 3, relatively minor surface area outflow flats 34 and 36 are recessed into the surface of the major area planar surface 22 in the region extending between the outflow hinge recess end edges 37 and 39, respectively, and the concave outflow edge 30 and the planar surface side edges 25 and 27, respectively. As shown in FIGS. 3 and 4, the outflow flat 36 is also bounded by extensions in the outflow direction 17 of the outflow open and closed stop side edges 41 and 42, respectively. The outflow flats 34 and 36 are preferably coplanar and are parallel with the laterally displaced outflow flats 34' and 36' formed in the diametrically opposed planar surface 22'. Alternatively, the outflow flats 34 and 36 may not be co-planar and not be parallel with the laterally displaced outflow flats 34' and 36' formed in the diametrically opposed planar surface 22'. In this alternative, at least the outflow hinge recess end edges 37 and 39 should be coplanar with one another and the outflow hinge recess end edges 37' and 39' should be co-planar with one another, so that the outflow end edges of each hinge recess 24, 26 and 34', 26' are consistent with respect to the major planar surfaces 22, 22'.

Figure 5:
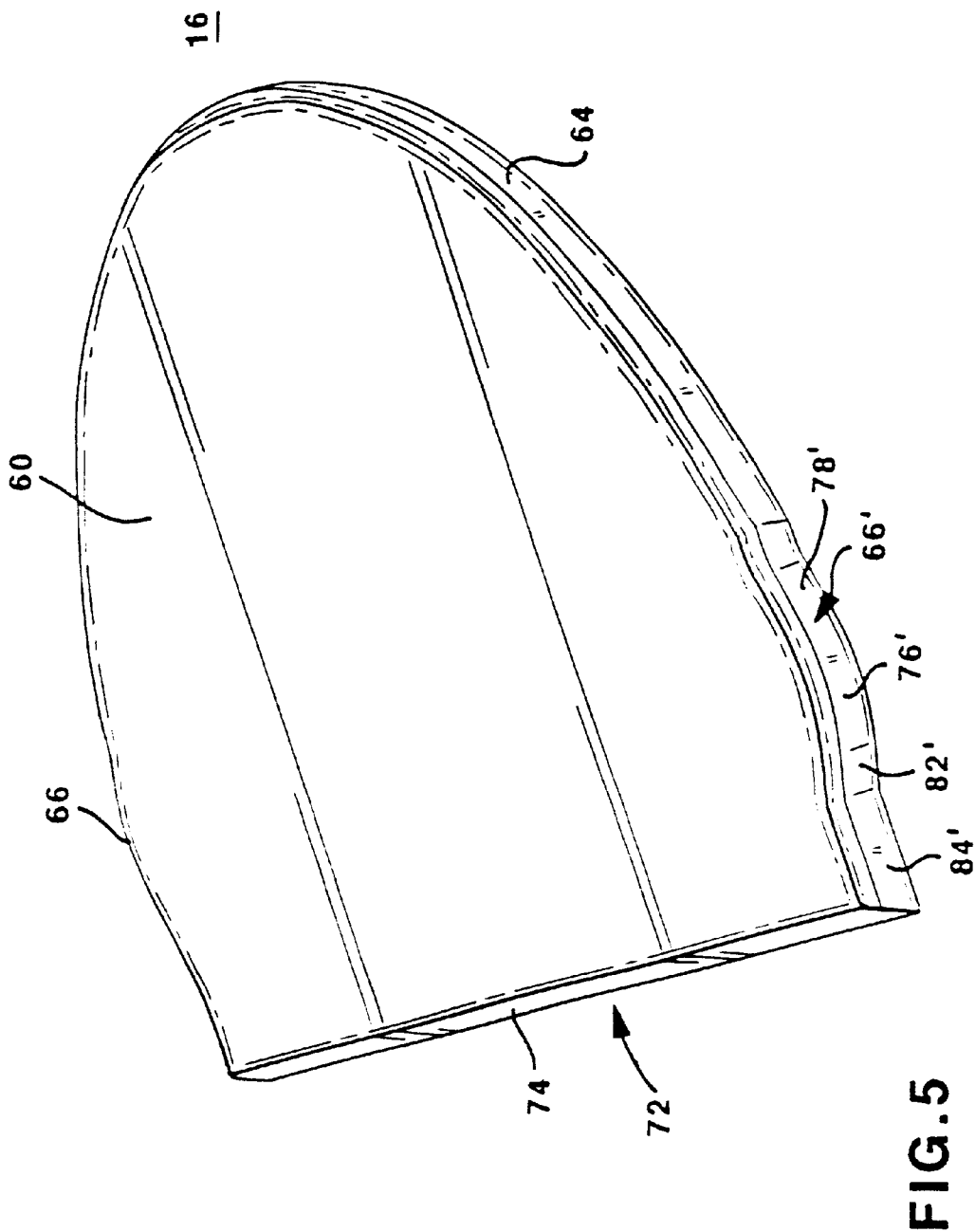
FIG. 5 is an isometric view of an exemplary planar valve leaflet viewed from the outflow surface thereof.
Figure 6:
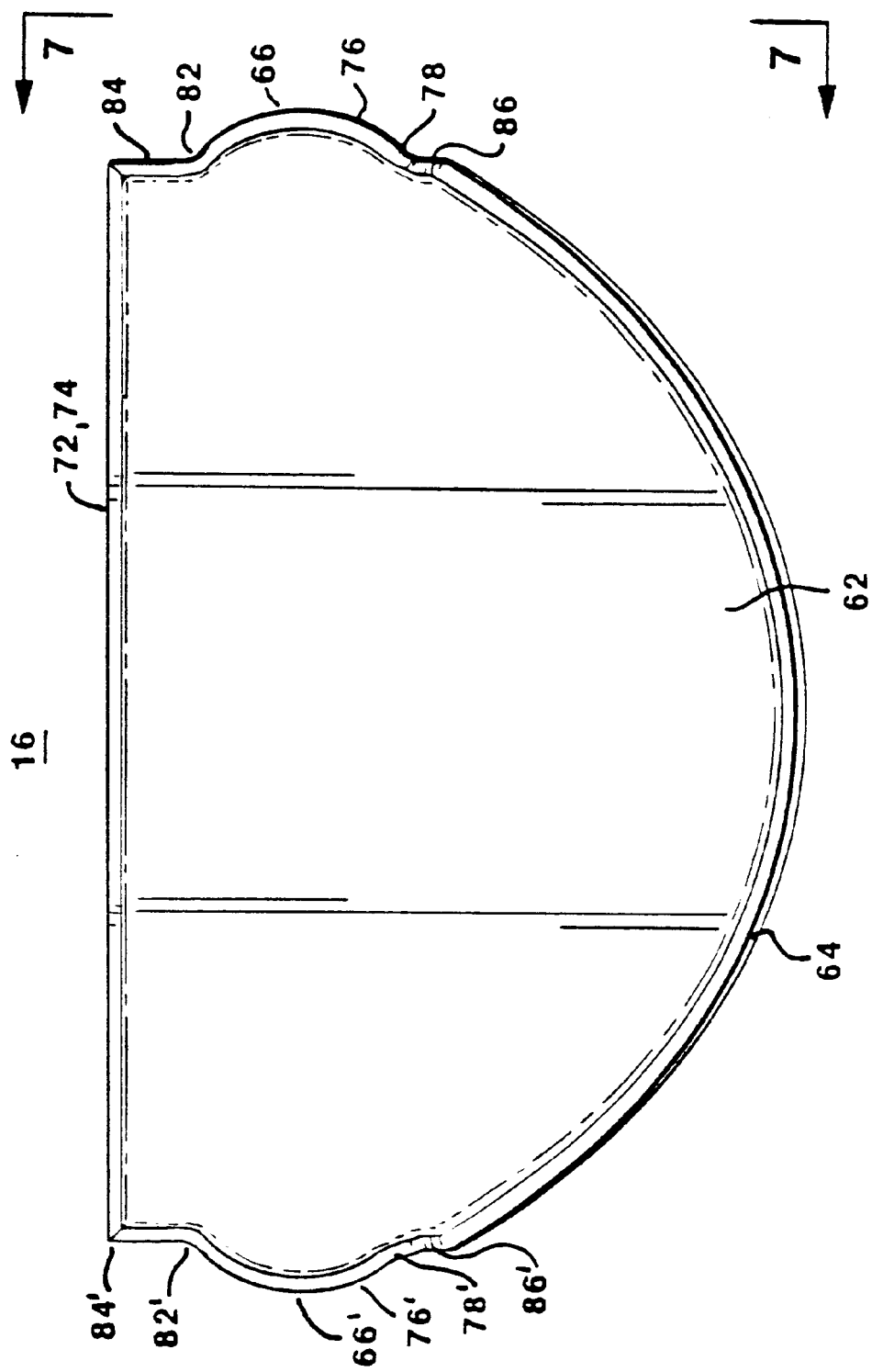
FIG. 6 is a plan view of the exemplary valve leaflet viewed from the inflow surface thereof.
Figure 7:
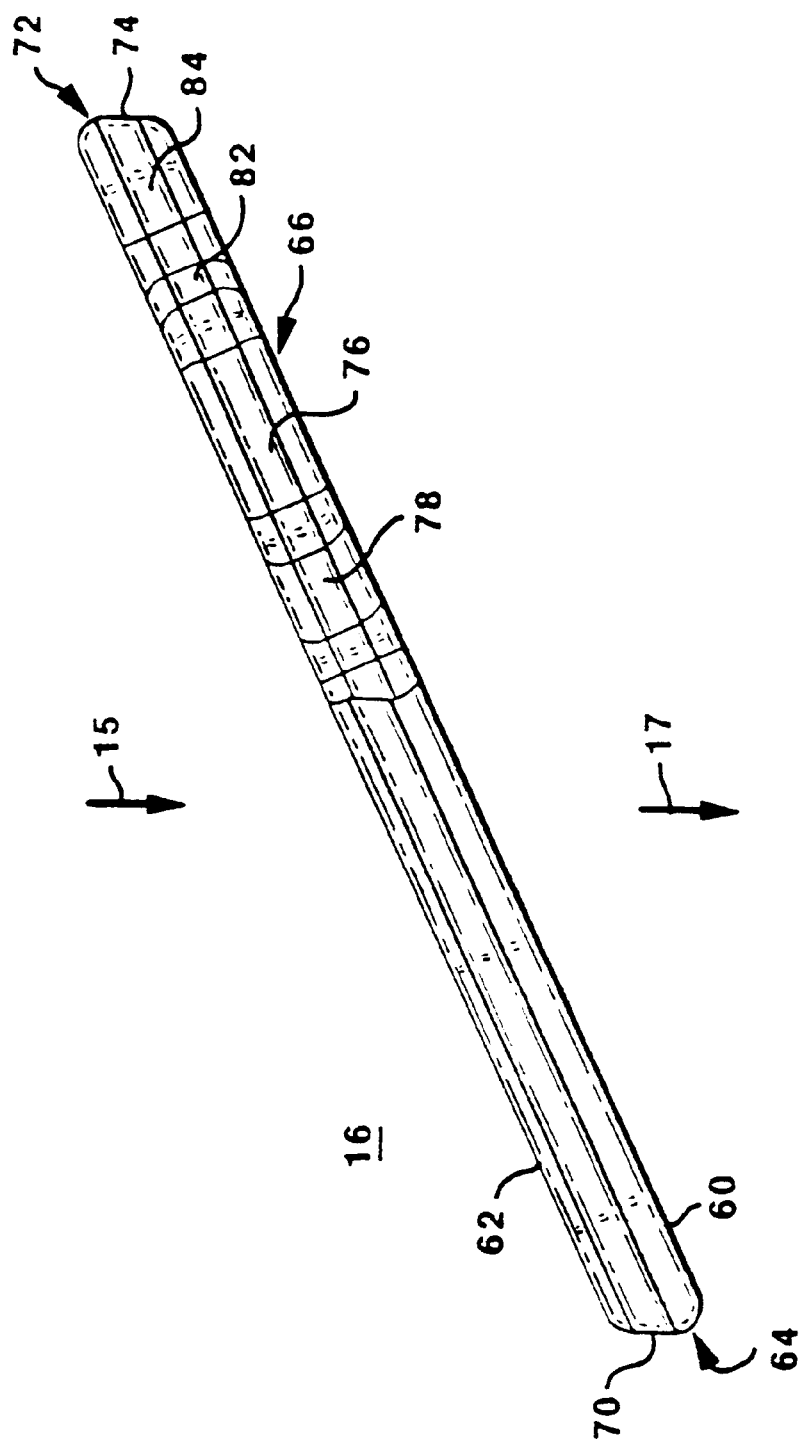
FIG. 7 is a side view of the planar valve leaflet taken from lines 7—7 of FIG. 6.

Turning to FIGS. 5, 6 and 7, they depict the valve leaflet 16, for example, in perspective, plan and side views taken from lines 7—7 of FIG. 6, respectively. The hinge recesses 26, 26' each receive a respective leaflet ear 66, 66' in the assembly of FIG. 1. Since the leaflets 14 and 16 are substantially identical to one another, only leaflet 16 is described in detail. The leaflet 16 is formed of a planar leaflet body having opposed inflow and outflow planar leaflet surfaces 62 and 60, respectively, and a continuous complex curvature peripheral edge joining the planar leaflet surfaces 60 and 62. A major curvilinear or arcuate exterior edge 64 extends between the opposed valve leaflets 66, 66' and forms the seating edge of the valve leaflet 16. As shown in FIG. 7, arcuate exterior edge 64 is beveled with bevel 70 at an angle to the valve body plane to form a fluid-tight fit against an arcuate seat region of the interior side wall 20 of the valve body 12 in the closed position. The valve leaflet 16 also is formed with a minor, generally straight interior edge 72 extending between the outwardly extending leaflet ears 66, 66' that is beveled with a bevel 74 at an angle to the valve body plane. The angle of bevel 74 is chosen so that the straight interior edge 74 of each leaflet 14 and 16 bear against one another in the closed position of the valve leaflets. The bevels 70 and 74 are radiused at their edges to merge smoothly with the inflow and outflow surfaces 62 and 60.

When the valve ears 66, 66' are fitted into the valve recesses 26, 26', the straight interior edge 72 extends transversely to the valve annulus centerline 11.

Retention and pivotal rotation of the valve ears 66, 66' in the valve recesses 26, 26' are achieved by the shape of the ears 66, 66' on the leaflet 16. Preferably, the ears 66, 66' are formed between the extremities of the arcuate exterior edge 64 and the ends of the straight interior edge 72.

The peripheral ear bearing edges 76, 76' of the leaflet ears 66, 66' are arcuate in profile and dimensioned to fit within the hinge recess profile 44 along the inflow recess bearing surface 54, the intermediate recess bearing surface 56 and the outflow recess bearing surface 58 depicted in FIG. 8 while allowing lateral translation therein as described below. The ear edge profile includes mirror image, curved outflow transition regions 78, 78' and relatively straight outflow shoulders 86, 86' between the opposite ends of the major arcuate peripheral edge 64 and the peripheral bearing edges 76, 76'. Mirror image, curved inflow transition regions 82, 82' are formed on the valve ear end and merge into straight inflow shoulders 84, 84' that are parallel to one another and terminate at the ends of the straight interior edge 72. The edges of each leaflet section and straight section are radiused to smoothly merge with the planar inflow and outflow surfaces 62 and 60. The distance between outflow shoulders 86 and 86' is greater than the distance between inflow shoulders 84 and 84'.

These distances are correlated to the distances between the opposed planar major surfaces 22 and 22' and between the opposed pairs of outflow flats 36 and 36' and 34 and 34'.

Figure 8:
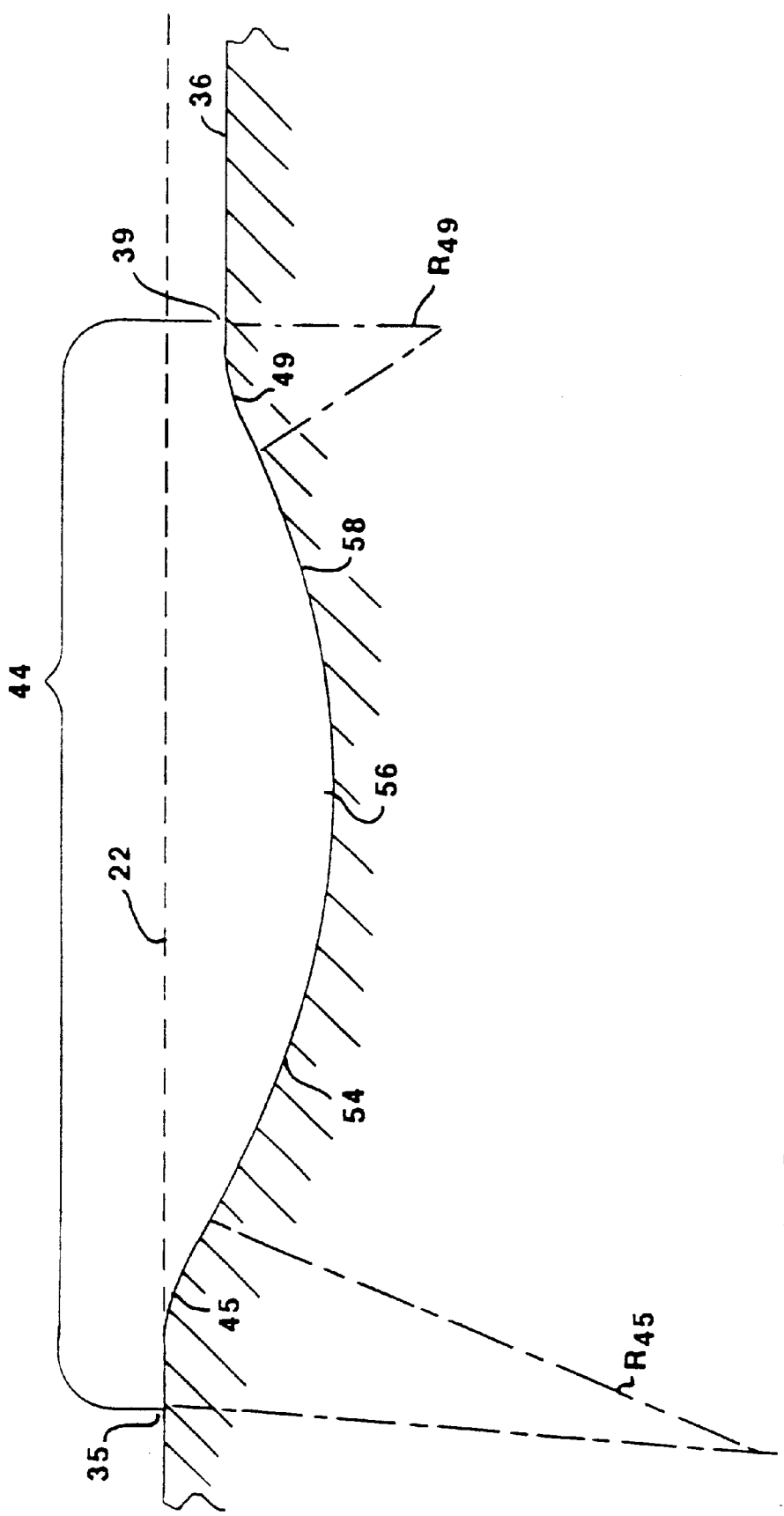
FIG. 8 is an elevation profile of the hinge recess bearing surface and the associated outflow flat taken along the normal angle of inclination ND of FIG. 4.

FIGS. 4 and 8 depict further details of the hinge recess bearing surfaces 54, 56 and 58 of the hinge recess 26 and the recess bearing surface profile 44 that are consistently also found in the other hinge recesses 24, 24' and 26'. The generally concave recess bearing surface profile 44 is observed in FIG. 8 in a section along the nominal angle of inclination ND of FIG. 4. The bearing surface profile 44 is asymmetric and complex in curvature characterized by convex curvature inflow and outflow transition surfaces 45 and 49 adjacent inflow and outflow hinge recess end edges 35 and 39, respectively, and concave inflow and outflow bearing surfaces 54 and 58 and intermediate bearing surface 56. From the inflow direction, the hinge recess bearing surface profile 44 commences at the inflow hinge recess end edge 35 adjacent planar surface 22 with the convexly curved inflow transition surface 45 and then concavely descends steeply in the inflow bearing surface 54 to a predetermined depth at intermediate bearing surface 56 between the opposed pivot points 50, 52. The asymmetric bearing surface profile 44 then becomes shallower in a concave outflow bearing surface 58 extending to the convex curvature outflow transition surface 49 at the boundary of the outflow end edge 39 and the outflow flat 36.

Each such hinge recess in the two opposed flat surfaces 22, 22' of the annular interior side wall 20 of the valve body 12 is much larger in the end-to-end direction along each of the angular directions CD, OD, and ND and more shallow in maximum depth at the intermediate bearing surface 56 than hinge recesses in any clinically used bi-leaflet heart valve designs known to the inventors. The larger and shallower hinge recesses of the present invention allow a lower blood pressure gradient to drive blood through the hinge recesses when the valve leaflets are in the transition and open positions and minimize blood stagnation therein.

The convex radius $R_{45}$ of curved inflow transition surface 45 is about two to three times greater than the convex radius $R_{49}$ of the curved outflow transition surface 49. For example, the convex radius $R_{45}$ is preferably in a range of about 0.020–0.050 inches, and the convex radius $R_{49}$ is preferably about two to five times smaller. The bearing surface profile 44 along the inflow recess bearing surface 54, intermediate bearing surface 56, and outflow bearing surface 58 is preferably an arc having a relatively constant radius greater than the radii $R_{45}$ and $R_{49}$. As shown below, the leaflet ear is formed having a slightly smaller radius.

The hinge recess bearing surface profile 44 depicted in FIG. 8 is somewhat asymmetric in depth by virtue of the recess of the outflow flat 36 below the major planar surface 22 and the differing radii of the inflow and outflow transition surfaces 45 and 49. The bearing surface profile 44 reveals that the inflow transition surface 45 is gradually sloped with a small inclination angle away from the major planar surface 22 to define a very shallow entrance ramp to admit blood flow into the hinge recess 26 in the inflow direction 15. The smooth and shallow entrance ramp into the more steeply descending and concave inflow bearing surface 54 creates a smooth path for the forward blood flow stream during the valve leaflet opening phase and also facilitates a reverse blood flow stream during the valve leaflet closing phase.

The bearing surface profile 44 of FIG. 8 also shows that the recess depth of the outflow flat 36 below planar surface 22 is less than the maximum depth of the hinge recess bearing surfaces in order to retain the valve leaflet ear therein. The decreased height of the outflow flat 36 at the outflow hinge recess end edge 39 and the adjacent curved outflow transition surface 49 allow blood funneled into the hinge recess 26 in the inflow direction 15 to more readily flow out again in the outflow direction 17. In other words, the recess depth of the outflow flat 36 below the planar surface 22 lowers the relative "dam" height of the outflow hinge recess end edge 39. The lowered height and the curved transition surface 49 adjacent thereto creates an open exit feature that takes advantage of a much smaller dynamic drag force acting on the opposed flat leaflet surfaces during the valve leaflet opening phase than exist during the valve leaflet closing phase. Any blood components located within the hinge recess can be easily washed out by the blood flow in both the inflow and outflow directions while the leaflet ears pivot about the pivot points 50 and 52 and the leaflet ear bearing edge sweeps across the inflow and outflow recess bearing surfaces 54 and 58 in both the opening and closing directions. In the opening and closing phases, the bearing edges 76, 76' of the convexly shaped leaflet ears 66, 66' projecting into the hinge recess 26 sweep the outer edges of the leaflet ears over the recess bearing surfaces 54, 56 and 58. The sweeping motion flushes blood components from the hinge recess 26 and into the outflow flat 36 and from the outflow flat 36 through the outflow portion of the annular orifice of the heart valve 10. This function is carried out in the same manner for each of the other three hinge recesses 24, 24' and 26'.

FIGS. 9 and 10 are elevation profiles depicting an exemplary leaflet ear 66 bearing against the hinge recess bearing surfaces 54, 56, 58 of exemplary hinge recess 26 taken in the opening and closing phases of the valve leaflet, respectively. FIGS. 9 and 10 show a small gap exists between the hinge recess bearing surfaces 54, 56 and 58 and the bearing edge 76 of the leaflet ear 66. Further small gaps are depicted between the inflow shoulder 84 and the planar surface 22 as well as between the outflow shoulder 86 and the outflow flat 36. The leaflets 14, 16 can laterally translate between the opposed hinge recess pairs 24, 24' and 26, 26' as a function of the depicted gaps. It is possible that contact may occur between at least one of the inflow shoulders 84 or 84' and the adjacent planar surface 22 or 22', respectively, during at least a part of the opening and closing phase.

The hinge recess profile 44 and the arcuate profile of the leaflet ear 66 provides controlled pivoting and translation movement of each valve leaflet 14 and 16 into the closed, seated position and the open position. The leaflet 14, 16 translates in the blood inflow direction as shown in FIG. 9 during the opening phase as the leaflet ear 66 rotates about the pivot point 50 in response to the blood pressure gradient and inflow of blood in the inflow direction 15. The translation is halted by the abutment of the leaflet ear outflow transition region 78 against the outflow transition surface 49 as shown in FIG. 9. Similarly, the leaflet 14, 16 translates back in the blood backflow direction as shown in FIG. 10 during the closing phase as the leaflet ear 66 rotates about the pivot point 52 in response to the diminution and reversal of the blood pressure gradient and backflow of blood against the inflow direction 15. The leaflet translation is halted by the abutment of the leaflet ear inflow transition region 82 against the inflow transition surface 45 as shown in FIG. 10. The leaflet translation before closing reduces its rotating arm and decreases the tangential velocity at the midpoint of the semi-circular exterior edge 64.

Referring back to FIG. 4, the translation of the leaflet also decreases the area of contact of the leaflet inflow ear side with the inflow, closed stop, side wall 42. This area of contact is already diminished by the formation of the outflow flat 36 across the inflow, closed stop, side wall 42. The reduction of this area of contact is desirable, because the largest proportion of blood cell damage in the hinge recess due to hinge function in each cardiac cycle occurs when the leaflet ear contacts the inflow closed stop side edge 42.

Thus, in the sweeping of the leaflet ears between the open and the closed positions, the leaflet rotation about pivot points 50 and 52 accelerates and decelerates as the leaflets approach the open and closed positions. The reduction in velocity in leaflet movement to the closed position reduces impact force of contact of the leaflet's peripheral seat exterior edge with the seat region around the respective half of the annular interior side wall 20 of the valve body 12. This reduced impact force prolongs the heart valve fatigue life and reduces the propensity of cavitation and valve closing noise. The large surface area of contact of the leaflet hinge ear bearing edges 76, 76' with the relatively wide inflow transition surface 45 and inflow recess bearing surface 54 of the hinge recess 26 also reduces concentrated valve leaflet closing stress on the hinge recess 26.

The reduced dam height of the outflow flats 34, 36 and 34', 36' also provides for a leakage of blood cells when the valve leaflets are closed that aids in washing of the associated hinge recesses 24, 26 and 24', 26'. During the valve leaflet closed phase, the blood pressure gradient reverses, and the reverse blood pressure gradient between the inflow side and the outflow side is much larger than that during the valve leaflet open phase. The relatively greater pressure gradient drives a minute leakage flow of blood through the hinge gap between the bearing surfaces and the adjacent leaflet bearing edges. This leakage flow provides a very important washing function to maintain the hinge recess clean. However, the efficacy of the washing function depends on the pressure head and restriction that must be overcome in the closed hinge recess. The reduction of the hinge recess height along the outflow hinge recess end edge 39 opens the restriction and reduces the pressure head allowing leakage blood flow along the hinge recess bearing surfaces 54, 56, 58 enhancing the washing function.

Figure 12:
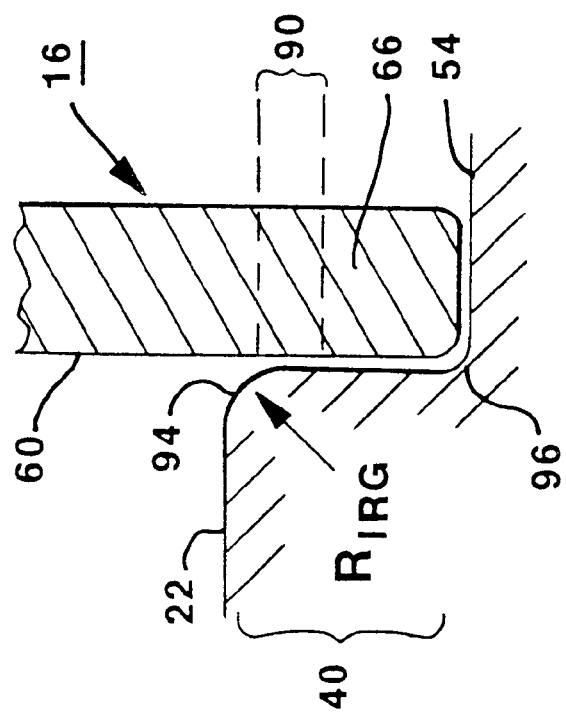
FIG. 12 is a depiction of the valve recess side wall and reduced area of contact with a leaflet ear side in accordance with a further aspect of the invention.
Figure 11:
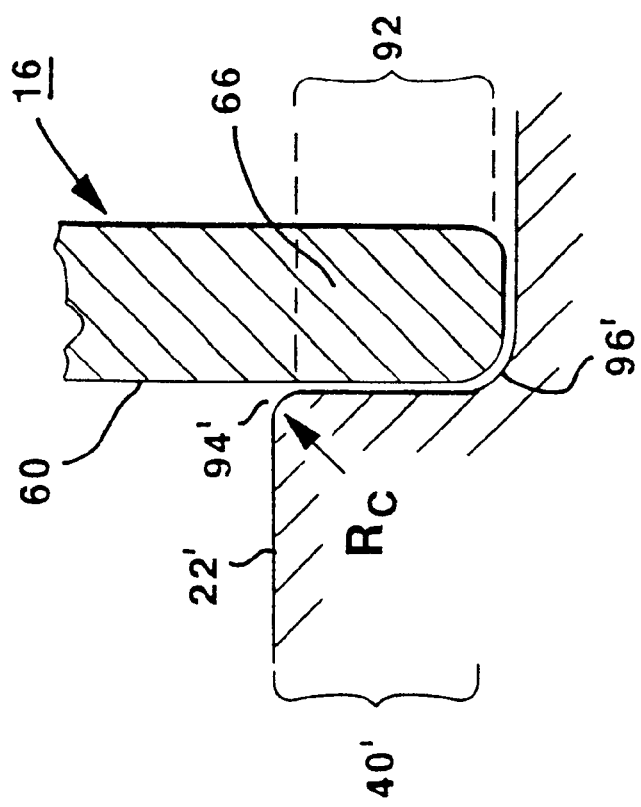
FIG. 11 is a depiction of a prior art valve recess side wall and area of contact with a leaflet ear side.

Turning to a further feature of the present invention, FIG. 11 depicts a prior art valve recess side wall and area of contact with a leaflet ear side, and FIG. 12 depicts the valve recess side wall and reduced area of contact with a leaflet ear side in accordance with a further aspect of the invention. The improved recess side wall configuration and its contact and the leaflet ear side depicted in FIG. 12 is described with respect to the outflow, closed stop, side wall 40 with the leaflet 16 in the closed position CD of FIG. 4, for example. However, it will be understood that this improved side wall configuration may be employed to form the inflow, closed stop, side wall 42 and to form the inflow and outflow, open stop, side walls 43 and 41.

In the improved recess side wall configuration of FIG. 12, the recess side wall 40 is shaped with a convex stop edge 94 at the junction of the side wall with the planar surface to provide a narrow contact line or band 90 of the recess side wall projecting into the hinge recess. A relatively dull, convex stop edge 94 is formed with a radius $R_{IRG}$ of preferably about 0.010–0.020 inches, and the side wall 40 is undercut at the edge 96 at the junction of the side wall 40 with the hinge recess bearing surface 54. The contact band 90 makes line or narrow band contact with the leaflet ear side of the outflow surface 60 to minimize the contact area in the closed position. The contact band 90 extends the length of the outflow, closed stop, side wall 40 to provide adequate stop area in the closed position of the leaflet. However, damage to blood components is reduced by the reduction of the surface area.

FIG. 11 depicts the prior art hinge recess side wall configuration known to us that is relatively planar between the relatively sharp edge 94' with a planar surface, e.g. planar surface 22', and the edge 96' with the hinge recess bearing surface, e.g. inflow recess bearing surface 54'. The edge 94' is formed with a radius $R_C$ of about 0.005 inches, for example. The relatively full contact between the opposed side wall 40' and the leaflet ear side wall in the contact area 92, for example, is intended. In variations on this approach, the radius of the edge 96' and the mating edge of the leaflet ear 66 may be increased from the depicted radii. In addition, the recess side wall may be angled at greater than the depicted 90° angle to the planar surface 22' to make contact with a corresponding angled leaflet ear surface. However, in each case, the relatively wide contact band 92 is maintained.

Returning to FIG. 1, the annular valve body 12 is configured as described above to support two, mirror image, valve-leaflets 14, 16 pivotally mounted in four such hinge recesses 24, 26 and 24', 26' in the two planar surfaces 22, 22'. The four hinge recesses 24, 26 and 24', 26' and the associated outflow flats 34, 36 and 34', 36' are arranged in a mirror image relationship of oppositely disposed hinge recess and associated outflow flat pairs with respect to a pair of arcuate seat regions of respective halves of the annular valve body 12.

Advantageously, in the open position, the leaflets 14 and 16 are held at an open angle of inclination OD which is slightly less than parallel to the inflow and outflow directions 15 and 17 and annular centerline 11. Specifically, this angle of inclination OD from the centerline axis of flow (the valve axis) is about ±4°. In the closed position, the valve leaflets are at the closed angles of inclination CD of about ±68°. Thus, at least a full ±60° pivotal range of motion is provided for the individual leaflets. The dual bi-leaflet configuration having a central opening with a relatively high flow area ratio and the steep angle of inclination CD greatly ameliorates the problems resulting from turbulence, regurgitation and eddy currents produced by several prior art valves.

The spacing apart of the oppositely disposed pairs of the hinge recesses 24, 24' and 26, 26' with respect to the centerline 11 and center plane provides for an optimized ratio of the central flow orifice in comparison to the two side flow orifices. The central flow orifice is defined by the axial flow area between the facing surfaces of the open valve leaflets 14, 16 and constitutes about 28–30% of the total orifice area. The side flow orifices are defined by the axial flow areas between the other surfaces of the valve leaflets 14, 16 and the opposed interior surface arcuate sections of the annular interior side wall 20 and together constitute about the remaining total orifice area. By contrast, commercially available bi-leaflet heart valves only provide central flow orifices providing about 20% of the total orifice area. The relatively larger central flow orifice causes the valve leaflets 14, 16 to be more sensitive to the local pressure gradient. For example, the leaflets 14, 16 can start to pivot to the closed position in response changes in the localized pressure gradient before reversal in the total pressure gradient occurs. This effect provides for less flow regurgitation, reduced leaflet impact force and noise on closure, and shorter leaflet closing time.

FIGS. 1–4 also depict further features of the present invention that enhance the hemodynamic blood flow characteristics of the valve, particularly the depicted aortic configuration thereof. The inflow rim 21 has a convex interior rim transition zone 21 that is optimized in radius to provide a smooth converging channel for blood flow in the inflow direction toward the annular orifice 13. The enhanced flare in the inflow rim transition zone 21' tends to deflect blood flowing in the inflow direction 15 toward the central flow orifice and away from the hinge mechanisms. A smaller radius outflow transition zone 23' is provided adjacent to the outflow rim 23. The smaller radius is necessary to avoid interference with the valve seat regions in the interior surface 22.

The inflow chamfer 29 is a flat surface formed between the concave inflow edge 28 of the planar surface 22 and the inflow rim 21 that tends to deflect blood flowing in the inflow direction 15 toward the central flow orifice and away from the hinge mechanisms. Similarly, the outflow chamfer 31 is a flat surface formed between the concave outflow edge 30 of planar surface 22 that deflects blood flow during the momentary reverse flow that occurs just before the valve leaflets close. These flat surface chamfers 29 and 31 are designed to deflect any platelet aggregates and microemboli away from the hinge mechanism during blood flow through the valve annular orifice 13. The planar surface 22 and the flat surface chamfers 29 and 31 effectively replace segments of the inflow rim transition zone 21' and the outflow rim transition zone 23'. The flat surface chamfers 29 and 31 avoid blood flow separation and thrombus formation sites that are attendant to the use of conical shaped chamfers of the type disclosed in the above-referenced '632 patent.

The preferred embodiment of the invention has been described above in the context of an aortic prosthetic valve design. In mitral prosthetic valve configurations, the profile of the valve assembly is altered in the manner shown in the above-incorporated '658 patent, for example. The resulting mitral valve body profile generally exhibits a depression in the inflow direction of opposed arcuate sections of the inflow rim 21 extending between the opposed planar surfaces 22, 22' and an extension of the valve body in the outflow direction. In reference to FIG. 3, the broken lines 80 and 81 approximately depict the relative heights and configurations of the inflow rim 21 and outflow rim 23, respectively, in these arcuate sections of the valve body 12, a mitral valve configuration.

As indicated above, the valve leaflet occluders respond hemodynamically to the natural pumping action of the heart, so as to alternately open and close so as to permit flow of blood through the valve annulus upon occurrence of an increase in pressure on the inflow side so as to cause a positive pressure differential relative to the outflow side. In the context of an aortic valve, for example, this occurs as the heart chamber on the inflow side contracts in the systolic phase following a diastolic phase during which it has filled with blood. Closure of the valve leaflets occurs at the end of the systolic phase as heart chamber relaxes and the relative outflow side blood pressure exceeds the inflow side blood pressure. Thus, during the transitions between the systolic and diastolic phases, the pressure reversal causes the leaflets 14 and 16 to pivot between their closed and open positions.

The leaflet hinge mechanism of the present invention decreases blood stagnation inside the hinge recesses and reduces the likelihood of blood components being trapped and damaged. Movement of the leaflets between the open and closed position causes the leaflet ears to sweep through the hinge recesses to wipe or flush blood components and microemboli out into the outflow flats and eliminate, or at least greatly reduce, the stagnation problems of prior art hinge mechanisms of this type. The compatible relationship between the leaflet ear bearing edges and the hinge recess bearing surfaces greatly enhances this wiping action. Such a compatible relationship may be attained with any configuration. A surface of revolution, however, is preferred and a spherical configuration most preferred.

Obviously, many modifications, and variations of the present invention are possible in light of the above teachings. For example, the assembly methods illustrated herein may be adapted to valves having a number of leaflets different from two or to leaflets of different configuration. The opening and closing angles of the leaflets relative to the flow axis are easily determinable by one of ordinary skill in the art. We have found that we can achieve a virtually full open position of the leaflets virtually in parallel with the central flow axis and still decrease their closing time and the associated regurgitation by increasing the central orifice blood flow ratio.

Sizing of the valve assembly and its various components, as well as tolerances therein, to provide adequate one-way valve operation—with a limited retrograde or reverse blood flow to provide a constant washing action and motion—are easily determinable by a person of ordinary skill in the art.

The present invention is particularly useful in a prosthetic heart valve coated in its entirety with pyrolytic carbon. The physical characteristics of pyrolytic carbon from the standpoint of strength and wear result in a highly desirable valve. Furthermore, pyrolytic carbon has been found to be highly compatible with blood and is relatively non-thrombogenic.

It is therefore to be understood, that within the scope of the appended claims, the invention may be practiced otherwise than as specifically described without actually departing from the spirit and scope of the present invention.

We claim:

1. A mechanical heart valve prosthesis comprising:
   an annular valve body having an interior side wall;
   at least one valve leaflet within the annular valve body; and
   a plurality of hinges, each hinge comprising:
      a hinge recess in the annular valve body interior side wall having a hinge recess bearing surface, the binge recess bearing surface including an inflow portion having an inflow recess bearing surface, and an outflow portion having an outflow recess bearing surface; and
      a leaflet ear having a leaflet ear bearing surface projecting from an edge of the at least one valve leaflet, the leaflet ear and hinge recess bearing surface being sized and shaped to flush blood from the hinge recess when the at least one valve leaflet moves;
   and wherein:
      an entrance ramp is defined in the inflow recess bearing surface to direct laminar blood flow into the hinge recess and over the inflow recess bearing surface as the leaflet ear bearing surface sweeps over the hinge recess bearing surface during movement of the valve leaflet between open and closed positions.

2. The heart valve prosthesis of claim 1, wherein the annular valve body comprises a pair of parallel, inwardly facing, opposed planar surfaces each bounded by planar surface edges, and wherein:
   the planar surfaces each have at least one hinge recess extending concavely outwardly from its planar surface into the annular valve body to a maximum depth and shaped to form the hinge recess bearing surface, each hinge recess having side edges shaped to define valve leaflet open and closed positions and each hinge recess having inflow and outflow hinge recess end edges extending between opposed ends of the hinge recess side edges and defining hinge recess boundaries; and
   the planar surfaces each have an outflow flat recessed therein that extends from each outflow hinge recess end edge in the outflow direction;
   whereby leaflet ears projecting into said hinge recesses allow said at least one valve leaflet to pivot between said open and closed positions and sweep the edges of said leaflet ears over said inflow and outflow hinge recess bearing surfaces and flush blood components from said hinge recesses into said outflow flats.

3. The heart valve prosthesis of claim 2, wherein the outflow flats are recessed into said planar surface to a flat recess depth less than the maximum depth of the hinge recess.

4. The heart prosthesis of claim 3, wherein an outflow transition surface is formed adjacent to said outflow hinge recess end edge to provide an exit ramp to facilitate blood flow from the outflow hinge recess end edge.

5. The heart valve prosthesis of claim 1 wherein said annular valve body is formed with an annular interior surface extending between an inflow rim and an outflow rim and a pair of parallel, inwardly facing, opposed planar surfaces formed along the annular interior surface of said annular valve body and each bounded by planar surface side edges and planar surface inflow and outflow edges; and further comprising: a planar inflow chamfer extending from said inflow rim to said planar surface inflow edge for deflecting any blood components susceptible of damage by operation of said hinges away from said hinges and centrally through said prosthesis during blood flow therethrough.

6. The heart valve prosthesis of claim 1, wherein;
   said annular valve body is formed with an annular interior surface and a pair of parallel, inwardly facing, opposed planar surfaces formed along the annular interior surface of said annular valve body and each bounded by planar surface edges, and
   the planar surfaces each having at least one said hinge recess forming at least one hinge recess pair with a first hinge recess on one planar surface and a second binge recess on a second, opposed planar surface, the first hinge recess of the hinge recess pair extending concavely outwardly from the one planar surface and into said annular valve body to a maximum depth and shaped to compliment and to form a first recess bearing surface for receiving a first one of said leaflet ear of the at least one valve leaflet and the second binge recess of the hinge recess pair extending concavely outwardly from the second planar surface and into said annular valve body to a maximum depth and shaped to compliment and to form a second recess bearing surface for receiving a second one of said leaflet ear of the at least one valve leaflet, each of the first and second hinge recesses of the hinge recess pair having side edges shaped to define leaflet open and closed positions and having inflow and outflow hinge recess end edges extending between opposed ends of the hinge recess side edges and defining hinge recess boundaries, whereby the first and second leaflet ears of the at least one valve leaflet projecting into said first and second hinge recesses, respectively, allow said leaflet to pivot between said open and closed positions and sweep the leaflet ear bearing surfaces over said inflow and outflow recess bearing surfaces and flush blood components from said hinge recesses into outflow flats recessed in the planar surfaces.

7. The heart valve prosthesis of claim 6, wherein the entrance ramp extends along the inflow hinge recess end edge as a convexly curved inflow transition surface merging into a concavely curved inflow recess bearing surface to the recess maximum depth.

8. The heart valve prosthesis of claim 7, wherein the outflow portion comprises a ramped recess bearing surface increasing in depth from the outflow flat and extending along the outflow binge recess end edge through a convexly curved outflow transition surface and a concavely curved outflow recess bearing surface to the recess maximum depth.

9. The heart valve prosthesis of claim 8, wherein the convexly curved inflow transition surface has an inflow radius of curvature and the convexly curved outflow transition surface is curved at an outflow radius of curvature that is less than the inflow radius of curvature.

10. The heart valve prosthesis of any one of the preceding claims 2, 3, 4, 5, 6, 7, 8 further comprising:
  a pair of generally convex outflow transition surfaces between an outflow rim and said annular interior side wall, and having a first radius of curvature; and
  a pair of generally convex inflow transition surfaces formed each extending in a band between an inflow rim and said annular interior side wall and between said opposed planar surfaces, each convex inflow transition surface having a second radius of curvature greater than said first radius of curvature.

11. A mechanical heart valve prosthesis comprising:
  an annular valve body having an interior side wall;
  at least one valve leaflet within the annular valve body; and
  a plurality of hinges, each hinge comprising:
    a hinge recess in the valve body interior side wall having a hinge recess bearing surface, the hinge recess bearing surface including an inflow portion having an inflow recess bearing surface, and an outflow portion having an outflow recess bearing surface; and
    a leaflet ear having a leaflet ear bearing edge projecting from an edge of the leaflet, the leaflet ear bearing edge and hinge recess bearing surface being sized and shaped to flush blood from the recess when the leaflet moves;

and wherein an outflow flat extends from each outflow recess bearing surface in the outflow direction,
whereby the leaflet ear bearing edge sweeps over said recess bearing surface and flushes flood components from said outflow hinge recess into said outflow flat as the leaflet moves between a closed and an open position.

12. The heart valve prosthesis of claim 11, wherein each of said valve recesses is further characterized by an inflow portion defining a ramped recess bearing surface increasing in depth from a planar surface and extending along the inflow hinge recess end edge through a convexly curved inflow transition surface into a concavely curved inflow recess bearing surface to the recess maximum depth whereby blood flowing in the inflow direction is swept in a laminar flow over the inflow hinge recess end edge and through the inflow portion.

13. The heart valve prosthesis of claim 12, wherein each of said hinge recesses is further characterized by the outflow portion defining a further ramped recess bearing surface increasing in depth from said outflow flat and extending along an outflow hinge recess end edge through a convexly curved outflow transition surface and whereby blood flowing in the outflow direction is swept over the outflow hinge recess end edge.

14. The heart valve prosthesis of claim 13, wherein said convexly curved inflow transition surface is curved at an inflow radius of curvature and said convexly curved outflow transition surface is curved at an outflow radius of curvature that is less than said inflow radius of curvature.

15. The heart valve prosthesis of claim 14, wherein said outflow flat is recessed to a flat recess depth that is less than the recessed maximum depth of the hinge recess into said planar surface, whereby the valve leaflet ear is retained in the hinge recess, and the decreased height of the outflow hinge recess end edge and said convexly curved outflow transition surface allows blood funneled into the inflow portion in the inflow direction to more readily flow out of the outflow portion into the outflow flat in the outflow direction.

16. The heart valve prosthesis of claim 13, wherein said inflow portion has an inflow recess bearing surface area and said outflow portion has an outflow recess bearing surface area less than said inflow recess bearing surface area.

17. The heart valve prosthesis of any one of the preceding claims 11–16, wherein;
  said leaflet comprises first and second leaflet ears each having an arcuate peripheral leaflet ear bearing edge extending convexly outward and dimensioned to fit within respective first and second hinge recesses forming an opposed pair of hinge recesses so that the arcuate peripheral leaflet ear bearing edge contacts the inflow recess bearing surface and the outflow recess bearing surface of the opposed pair of hinge recesses while allowing lateral and pivotal translation therein; and
  said leaflet comprises:
    first and second relatively straight outflow shoulders extending between opposite ends of a major arcuate peripheral edge of the leaflet and the arcuate peripheral leaflet ear bearing edge of the first and second leaflet ears, respectively, whereby the first and second outflow shoulders are separated apart by a first distance sufficient to locate said first and second shoulders between a pair of opposed outflow flats; and
    first and second relatively straight inflow shoulders extending between opposite ends of a straight peripheral edge of the leaflet and the ear bearing edge of the first and second leaflet ears, respectively, whereby the first and second inflow shoulders are separated apart by a second distance less than said first distance sufficient to locate said first and second shoulders between a pair of opposed planar surfaces on the annular valve body.

18. The heart valve prosthesis of any one of the preceding claims 12–16, wherein each of said leaflet ears has a leaflet ear inflow side and a leaflet ear outflow side, and further comprising:

a closed stop associated with each of said hinge recesses for defining a closed leaflet position, said closed stop comprising an inflow closed recess side wall and an outflow closed recess side wall in each hinge recess, said inflow and outflow closed recess side walls positioned for engaging against said leaflet ear inflow and outflow sides, wherein said inflow and outflow closed recess side walls are shaped with a convex stop edge at a junction of each of said inflow and outflow closed recess side walls with the planar surface on the annular valve body to provide a contact band portion for each of the inflow and outflow closed recess side walls, the contact band portions projecting into said hinge recesses to minimize the contact area between the contact band portions and said leaflet ear inflow and outflow sides when the leaflet is in the closed leaflet position.

19. The heart valve prosthesis of any one of the preceding claims 2–16, wherein each of said leaflet ears has a leaflet ear inflow side and a leaflet ear outflow side, and further comprising:

a closed stop associated with each of said binge recesses for defining a closed leaflet position, said closed stop comprising an inflow closed recess side wall and an outflow closed recess side wall in each hinge recess, said inflow and outflow closed recess side walls positioned for engaging against said leaflet ear inflow and outflow sides, wherein said inflow and outflow closed recess side walls are shaped with a convex stop edge at a junction of each of said inflow and outflow closed recess side walls with the planar on the annular valve body to provide a contact band portion for each of the inflow and outflow closed recess side walls, the contact band portions projecting into said hinge recesses to minimize the contact area between the contact band portions and said leaflet ear inflow and outflow sides when the leaflet is in the closed leaflet position; and an open stop associated with each of said hinge recesses for defining an open leaflet position, said open stop comprising an inflow open recess side wall and an outflow open recess side wall in each hinge recess, said inflow and outflow open recess side walls positioned for engaging against said leaflet ear inflow and outflow sides, wherein said inflow and outflow open recess side walls are shaped with the convex stop edge at a junction of each inflow and outflow open recess side wall with the planar surface of the annular valve body to provide the contact band portion for each inflow and outflow open recess side walls, the contact band portions projecting into said hinge recesses to minimize the contact area between the contact band portions and said leaflet ear inflow and outflow sides when the leaflet is in the open leaflet position.

* * * * *

UNITED STATES PATENT AND TRADEMARK OFFICE
CERTIFICATE OF CORRECTION

PATENT NO.    : 6,645,244 B2
DATED         : November 11, 2003
INVENTOR(S)   : Shu et al.

It is certified that error appears in the above-identified patent and that said Letters Patent is hereby corrected as shown below:

Column 17,
Line 63, change "the binge recess" to read -- the hinge recess --

Column 18,
Line 64, change "a second binge" to read -- a second hinge --

Column 19,
Line 32, change "outflow binge recess" to read -- outflow hinge recess --

Column 21,
Line 28, change "claims 2-16" to read -- claims 12-16 --

Signed and Sealed this

Sixth Day of July, 2004

JON W. DUDAS
*Acting Director of the United States Patent and Trademark Office*